US006303148B1

(12) United States Patent
Hennink et al.

(10) Patent No.: US 6,303,148 B1
(45) Date of Patent: Oct. 16, 2001

(54) PROCESS FOR THE PREPARATION OF A CONTROLLED RELEASE SYSTEM

(75) Inventors: Wilhelmus Everhardus Hennink, Waddinxveen; Okke Franssen, Utrecht, both of (NL)

(73) Assignee: Octoplus B.V., Leiden (NL)

( * ) Notice: Subject to any disclaimer, the term of this patent is extended or adjusted under 35 U.S.C. 154(b) by 0 days.

(21) Appl. No.: 09/308,349

(22) PCT Filed: Nov. 17, 1997

(86) PCT No.: PCT/NL97/00625

§ 371 Date: Aug. 17, 1999

§ 102(e) Date: Aug. 17, 1999

(87) PCT Pub. No.: WO98/20093

PCT Pub. Date: May 28, 1998

(30) Foreign Application Priority Data

Nov. 19, 1996 (EP) .................................................. 96203234

(51) Int. Cl.⁷ ................................. A61K 9/14; A61K 9/16
(52) U.S. Cl. .......................... 424/489; 424/490; 424/496; 424/497
(58) Field of Search ................................... 424/423, 489, 424/490, 496, 497

(56) References Cited

U.S. PATENT DOCUMENTS 4,963,367  * 10/1990  Ecanow ................................. 424/485
5,674,521  * 10/1997  Gehrke et al. ....................... 424/423
5,980,948  * 11/1999  Goedemoed et al. ............... 424/489

FOREIGN PATENT DOCUMENTS 0 213 303 A2  * 11/1987 (EP) .

OTHER PUBLICATIONS

De Smedt et al. "Characterization of the Network Structure of Dextran Glycidyl Methacrylate Hydrogels by Studying the Rheological and Swelling Behavior", Macromolecules 28, (1995) 5082–5088.

Gehre et al. "Enhanced Loading and Activity Retention of the Proteins in Hydrogel Delivery Systems", Proceed. Intern. Symp. Control. Rel. Bioact. Mater., 22 (1995) 145–146.

Heller et al. "Controlled Release of Water–Soluble Macromolecules from Bioerodible Hydrogels", Biomaterials 4 (1983) 262–266.

(List continued on next page.)

*Primary Examiner*—Thurman K. Page
*Assistant Examiner*—S. Tran
(74) *Attorney, Agent, or Firm*—Morrison & Foerster

(57) ABSTRACT

A process for the preparation of a controlled release system, comprising forming of an aqueous two-phase system form at least two water soluble polymers which are incompatible in solution, at least one of these polymers being cross-linkable, the cross-linkable polymer phase being emulsified in the other polymer phase; adding at least one releasable compound which is soluble in the cross-linked polymer phase in the aqueous solution, allowing the releasable compound to diffuse in the cross linkable polymer phase; cross-linking the cross-linkable polymer before or after the releasable compound is added, preferably to a degree that the pores in the cross-liked structure are substantially smaller than the particle size of the releasable compound; and separating the cross-linked structures enclosing the release able compound from the other phase. Further, the invention relates to microspheres, at least 80 wt. % thereof having a particle size of between 100 nanometers and 1000 um, which microspheres are comprised of a degradable, cross-linked polymer encapsulating at least one releasable compound, the pore size of the cross-linked polymer being smaller than the particle size of the releasable compound.

17 Claims, 9 Drawing Sheets

OTHER PUBLICATIONS

Hennink et al. "Controlled Release of Proteins from Dextran Hydrogels", Journal of Controlled Release 39 (1996), 47–57.

Kim et al. "Hydrogels: Swelling, Drug Loading and Release", Pharmaceutical Research 9(3) (1992) 283–290.

M. Bradford, "A Rapid and Sensitive Method for the Quantitation of Microgram Quantities of Protein Utilizing the Principle of Protein–Dye Binding", Anal. Biochem. 72 (1976) 248–254.

Van Dijk–Wolthius et al. "Synthesis Characterization and Polymerization of Glycidyl Methacrylate Derivatized Dextran", Macromolecules 28, (1995), 6317–6322.

* cited by examiner

Figure 6

Effect of mixing technique on particle size

▲ Mechanical Stirring
▼ Vortex

PROCESS FOR THE PREPARATION OF A CONTROLLED RELEASE SYSTEM

The present invention relates to a process for the preparation of a system having good controlled release behaviour, and to microspheres with a good controlled release behaviour.

The fast developments in the biotechnological field lead to a large number of pharmaceutically interesting products, esp. proteins, peptides and genes. Such products can suitably be used in the treatment of life-threatening diseases, e.g. cancer, and several types of viral, bacterial and parasital diseases.

Due to their nature, proteins and proteinaceous products, e.g. peptides, which group of products will be referred to as protein drugs herein-below, cannot efficiently be administered orally. They have to be brought in the system parentally, i.e. by injection. The pharmacokinetical profile of these products is such that injection of the product per se requires a frequent administration. In other words, since protein drugs are chemically and physically unstable in the gastro intestinal tract and generally have a short active residence time in the human or animal body, multiple injections in a short time are required to attain a therapeutic effect. It will be evident that this is inconvenient for patients requiring these protein drugs.

For this reason, there is a need for delivery systems which have the capacity for sustained release. A number of options have been proposed in the art, while synthetic biodegradable, rather well-defined polymers are used to control the release of encapsulated drugs.

One of the options described in the prior art is the use of microspheres and nanospheres made of polymers. These microspheres or nanospheres are spherical particles, spherical capsules, nanocapsules or nanoparticles having a particle diameter between about 0.1 $\mu$m and about 100 $\mu$m. In this description and the claims, the reference to microspheres also encompasses microparticles, microcapsules, nanospheres, nanoparticles and nanocapsules. Widely used polymers to prepare these microspheres are poly lactic acid and copolymers of lactic acid with glycolic acid. The polymers should preferably be biodegradable to avoid removal of the polymer carrier after use.

The hitherto known preparation methods for drug containing controlled or sustained release systems generally involve the use of organic solvents. Organic solvents may lead to structural changes in protein structure, esp. in the secondary and tertiary structure. Such changes may lead to a denaturation of the protein drug. Since these structural changes normally lead to a loss in pharmacological activity and the occurrence of undesired side-effects, such changes are undesirable, as will be apparent. Moreover, the use of organic solvents is not desirable from and environmental point of view, either.

Further, it is hardly possible to avoid that traces of organic solvents will remain in or on the microspheres produced. Especially, when toxic solvents are used, such as the widely applied solvents chloroform and dichloromethane, this is a problem.

Another problem is that it is difficult to encapsulate proteins in polymeric matrices in a reproducible way. It is of the utmost importance that predictable and reproducible amounts of proteins or other encapsulated products to be used as drugs are released.

Hydrogels have also been used in the preparation of delivery systems for protein drugs. One of these systems comprises crosslinked dextrans obtained by radical polymerization of glycidyl methacrylate derivatized dextran (dex-GMA). In this respect, reference is made to Van Dijk-Wolthuis et al. in Macromolecules 28, (1995), 6317–6322 and to De Smedt et al. in Macromolecules 28, (1995) 5082–5088.

It appeared that the release of the proteins from these hydrogels depends on and can be controlled by the degree of crosslinking and the initial water content of the gel (Hennink et al., J. of. Contr. Rel. 39 (1996), 47–57).

Encompassed drugs are released from these hydrogels or polymeric microspheres during biodegradation of the polymeric material and/or by diffusion.

Drugs are usually loaded into hydrogels or microspheres derived hereof either by equilibration in a drug-containing solution followed by drying (see e.g. Kim et al. in Pharm. Res. 9(3) (1992) 283–290) or by incorporation of the drug during the preparation of the hydrogel or microspheres (see e.g. Heller et al. in Biomaterials 4 (1983) 262–266). Both techniques have a number of disadvantages other than those arising from any organic solvents used.

Loading by equilibration normally leads to a rather low drug content in the delivery system. This is especially the case, when the drug is a macromolecular compound. Unless the pore size of the hydrogel or the microspheres is rather large, the macromolecules will only adsorb onto the outer surface, which may, after application, lead to a burst release in the human or animal system. Further, the solvent phase containing the drug, which phase is contacted with the delivery system to load the delivery system, has to be removed from the hydrogel or the microspheres. This can produce the migration of the drug to the surface of the delivery system, and hence to a non-homogeneous drug distribution. This tends to result in a significant burst release of the drug, as well, which generally is not desired.

A suitable loading process for incorporating macromolecular drugs is aimed at.

In an article in Proceed. Intern. Symp. Control. Rel. Bioact. Mater., 22 (1995), 145–146, Gehrke et al. have described a technique wherein loading levels higher than obtainable by solution sorption, hence higher than about 0.1 wt. %, can be achieved in purified, pre-formed hydrogels. The loading technique is based on the fact that certain polymer mixtures split into separate phases when dissolved in water. Proteins dissolved in such a system distribute unevenly between the phases. This principle also holds when one of the polymer phases is a crosslinked gel.

In particular, Gehrke et al. describe a crosslinked dextran gel/poly (ethylene glycol) system, and a crosslinked hydroxypropylcellulose gel/poly (vinyl alcohol) system. Proteins present in an aqueous solution containing beads of the gel are, after the addition of the non-crosslinked second polymer, adsorbed on the beads and partly absorbed through meshes or pores in the bead surfaces.

A disadvantage of this technique is that the proteinaceous material is to a major extent only adsorbed to the beads, which means that if the phase containing the second polymer is replaced by another aqueous system a fast removal of the proteins from the beads is observed. Only when large amounts of pores having a diameter larger than the size of the proteinaceous material to be loaded are present in the bead surfaces, some absorption may occur. This adsorption and limited absorption behaviour has an undesirable effect on the release of the proteinaceous material from the beads.

To additionally illustrate the undesired release behaviour, it is noted that the profiles shown in the article are—from a pharmacological point of view—entirely unsuitable to be used in controlled release systems. Moreover, the gel beads are too large (cylinders with a diameter of 1.5 mm) to be suitably used for administration in the human or animal body.

In EP-A-0 213 303 a method for producing spherical polymer particles from systems containing two liquid aqueous phases is described. One of the two phases is dispersed in the form of droplets in the other phase to form an emulsion. Subsequently, the droplets are caused to solidify. In the phase to be dispersed, a macromolecular substance may be dissolved. Further, low molecular substances such as medicaments, vaccines and insecticides can be chemically bonded to the particle forming substance in the dispersed phase. Nothing is being said about the release behaviour of the dissolved substance, nor over the application of the spherical polymer particles formed or the size thereof.

The principle of affinity partitioning in PEG-containing two-phase systems is also known from Göte Johansson, Affinity Partitioning in PEG-containing Two-phase Systems In: Topics in Applied Chemistry; Poly (ethylene glycol) chemistry, Biotechnological and Biomedical Applications, Ed. J. M. Harris, Plenum Press (1992). In this article, a two-phase system is described, which is created when an aqueous solution of dextran and polyethylene glycol (PEG) are mixed. A PEG enriched and a dextran enriched phase are formed. Proteins are partitioned unequally in such systems. These known systems are used in the purification of proteins.

The present invention is aimed at providing a new injectable, patient friendly delivery system for protein drugs, which system is safe and biodegradable, and which system possesses well controllable delivery kinetics. The period wherein drug delivery should be guaranteed depends on the protein drug used, and varies between a number of days upto more than one year. In addition, high degrees of loading in the delivery system should be obtained. Moreover, the system of the present invention should be produced without needing the use of organic solvents.

The problems mentioned above are solved by a specific preparation method of controlled release systems, such as microspheres, wherein water is used as the solvent. The use of water as sole solvent system is advantageous from an environmental point of view, because of toxicological considerations, and, especially, because of reasons of protein stability.

In a first aspect, the present invention relates to a process for the preparation of a controlled release system, comprising:
(a) forming of an aqueous two-phase system from two water soluble polymers and at least one releasable compound, the two water soluble polymers being incompatible in solution, at least one of these polymers being crosslinkable, the crosslinkable polymer phase being emulsified in the other polymer phase; and the at least one releasable compound being soluble in the crosslinkable polymer phase in the aqueous solution;
(b) allowing the releasable compound to dissolve or diffuse in the crosslinkable polymer phase; and
(c) crosslinking of the crosslinkable polymer, wherein step (b) can be carried out before or after step (c).

In a preferred embodiment, the crosslinking is carried out to such a degree that the pores (meshes) in the crosslinked structure eventually formed are substantially smaller than the size of the releasable compound. By emulsifying an aqueous crosslinkable polymer in a continuous phase comprised of water and a polymer which is not compatible with the crosslinkable polymer, and crosslinking the discontinuous phase, the particle size of the crosslinked polymer particles can be adjusted, while the particle size distribution can be narrow, as in described herein-below in more detail.

Hence, in a further aspect, the present invention is directed to microspheres, at least 80 wt. % thereof having a particle size of between 100 nanometer and 100 $\mu$m, which microspheres are comprised of a degradable, crosslinked polymer encapsulating at least one releasable compound, the pore size of the crosslinked polymer being equal or preferably smaller than the particle size of the releasable compound. These microspheres are obtainable by using the process of the invention, and are free from organic solvents. Dependent on the application of the microspheres, the size can e.g. be adjusted between 1 and 50 $\mu$m, preferably between 2 $\mu$m and 25 $\mu$m, such as between 5 and 15 $\mu$m.

When the pore sizes or meshes of the crosslinked polymer are equal or smaller than the hydrodynamic diameter size of the releasable component, the releasable component is essentially released when the polymer is degraded. More in particular, in this embodiment, the crosslinked structure must be degradable in the human or animal body, so that the encapsulated releasable compound can leave the crosslinked matrix. If on the other hand, the pore sizes or meshes of the crosslinked polymer are larger than the size of the releasable component, the releasable component is at least partially released by diffusion. The pore size of the crosslinked product obtained by the process of the present invention in this way provides a perfect tool to control the release. Further, the efficiency of the incorporation of a releasable compound in such a polymer structure is very high, while the degree of loading can be adjusted up to the saturation concentration of the compound to be released.

The degradability of the crosslinked structure can be regulated in a number of ways. As a first example, it is note that bonds can be incorporated, which are hydrolysable under physiological conditions. In this respect, reference can be made to the European patent application 96201821.4 of the group of the present inventors. This patent application teaches hydrogels comprising hydrolytically labile spacers between different polymer chains. The hydrolytically labile spacers described therein can be suitable used in the present invention and are incorporated herein by reference.

Another example to control the degradability is the coencapsulation of an enzyme or chemical substance capable of breaking bonds in the crosslinked polymer. In a preferred embodiment of the process of the present invention the crosslinkable polymer is a dextran polymer. In this embodiment a dextranase can be added to the aqueous two-phase system before the crosslinking step or added afterwards.

The dextran polymer can suitably be used in the process of the present invention together with a polyethylene glycol or Pluronic®, which is a preferred polymer to be used in the inventive process.

The product aimed at by the process of the present invention can be separated from the other polymer phase using conventional techniques, for instance centrifugation and decantation.

In a first step of the process of the present invention an aqueous two-phase system is formed. This two-phase system comprises water, and at least two water soluble polymers, which polymers are incompatible in solution. Preferably a compound to be released is also present, although it is possible to add the compound to be released after the crosslinking step. At least one of the polymers present in the aqueous phase is crosslinkable, and the crosslinkable polymer phase is emulsified in the other aqueous polymer phase.

The polymers used can be chosen dependent on the nature of the compound to be released. It is preferred that the compound to be released will have a clear preference for the crosslinkable polymer phase. In that case, the highest possible degree of loading, theoretically up to the saturation concentration, in the microspheres to be made, can be obtained.

It is not critical which crosslinkable polymer is used. However, if the controlled release system comprising the polymer in crosslinked form is intended to be brought into a human or animal body, the polymer should be pharmaceutically acceptable and preferably should be degradable. Suitable crosslinkable water soluble polymers are dextrans and derivatized dextrans, starches and starch derivative, cellulose derivatives such as hydroxyethyl and hydroxypropyl cellulose, polyvinylpyrrolidone, proteins and derivatized proteins, and so on. The molecular weigth of the crosslinkable polymers used normally lies between 1,000 and 1,000,000 Da. It is noted that with a higher molecular weight of the polymer, a better phase separation is generally obtained in the aqueous solution used in the process of the invention.

The person skilled in the art will have the knowledge to choose the crosslinkable polymer and the crosslinking conditions required for the emulsion prepared. For instance, dextans can be crosslinked with methylacrylate or methacrylate groups. Another example is a system comprising PVP as the external phase and dextran as the emulsified phase, wherein the dextran is crosslinked through the presence of isocyanates.

Further, reference is made to crosslinking using radiation. Dex-GMA can e.g. be polymerized using small dosages of γ-radiation, such as less than 0.1 Mrad. An advantage of this embodiment is that in one step sterile microparticles can be obtained. Further, crosslinking by UV radiation and physical crosslinking using e.g. hydrophobic tails coupled to a polymer are possible techniques.

In a preferred embodiment, the crosslinkable polymer is a temperature sensitive polymer such as poly-N-isopropyl-acrylamide, which polymer can, e.g., be present as a graft on another polymer such as a dextran. Hydrogels of these polymers show increasing swelling behaviour at degreasing temperatures. This makes it possible that releasable material can easily penetrate in the hydrogel after the crosslinking reaction. By subsequently raising the temperature, e.g. to a value of 37° C., the meshes in the hydrogel shrink, thereby capturing the releasable compound.

The polymer which is present in the aqueous continuous phase can be any polymer which is incompatible with the crosslinkable polymer. Although this polymer may also be crosslinkable, but of course not under the reaction conditions used for the crosslinking of the discontinuous polymer phase, this is not preferred. Examples of suitable polymers incompatible with the polymer to be crosslinked are poly (ethylene glycol) (PEG) and poly(vinyl alcohol) (PVA) (in combination with e.g. dextrans and dextran derivatives, starches and starch derivatives, PVP, and water soluble cellulose derivatives).

The release of the releasable compound depends on a number of variables, which can be used to tailor the delivery as desired. One of these variables is the size of the microspheres. The size can be adjusted by carefully modifying the process circumstances and formulation parameters in the emulsifying step. For instance, the water content, the presence of hydrophobic groups on any one of the polymers or mixtures of polymers used, the viscosity of the continuous and discontinuous phase, and the electrical charge on the at least two polymers used are examples of tools to adjust the size of the microspheres or microparticles to be produced. In addition, emulsifiers can be added. Suitable emulsifiers are copolymers, preferably block-copolymers, of units of the two incompatible polymers, e.g. a block-copolymer of PEG and dextran, used to create the two-phase system.

To further guarantee a controlled release, the crosslinked polymer should preferably be degradable.

As said herein-above, it is important that the two water soluble polymers are incompatible with one another, so that a two phase system is obtained after the two polymers have been added to each other in an aqueous solution. Whether or not a two phase system will be obtained depends not only on the nature of the two polymers involved, but also on the conditions under which they are added. Factors that are relevant in this regard are the molecular weight of the polymers, their concentrations in the aqueous solution, the temperature at which they are added to one another, and so forth. It is part of the standard skills of the artisan to determine a phase diagram for any combination of polymers that can be used, and thus to choose suitable conditions for obtaining a phase separation.

In the attached FIG. 9 a phase diagram of a water/PEG/dextran ternary system is shown as example. When the starting-composition is below the binodal (————), a one phase system is present, whereas above the binodal, two coexisting phases are formed: one enriched in polymer 1 (composition $x_1$) and other enriched in polymer 2 (composition $x_2$). $x_1$ and $x_2$ are connected via a tie-line (__). All systems prepared using starting-compositions on the same tie-line separate into phases of constant composition. For a given starting-composition, the volume ratio of the coexisting phases $x_1/x_2$ equals $y_2/y_1$.

As indicated herein-above, the releasable compound can be a protein drug. However, it is also possible to encapsulate pharmacon containing nanoparticles or microparticles, e.g. liposomes and iscoms. The encapsulation of this type of particles has the advantage of preventing the occurrence of a too fast release of the encapsulated compound, or, said in other words, burst-effects can be avoided in a more secure way.

The partition of the compound to be released is primarily determined by the nature of the polymers present in the aqueous two-phase system. This partition can be influenced, e.g. by adding salt to the aqueous system, or by adjusting the pH.

If the releasable compounds, such as proteins, are present during the crosslinking step, care should be taken that the integrity of the releasable compounds is secured. It should for instance be avoided that proteinaceous material is oxidized by initiator systems etc. In this light, it is noted that adverse effects can be avoided or minimized by minimizing the amount of initiator, reducing the polymerization time or adding suitable antioxidantia, such as α-tocopherol.

The separation of the crosslinked structures enclosing the releasable compound from the other phase can be carried out in any conventional way. Preferably, the separation is effected by filtration or centrifugation. The crosslinked structures can subsequently be washed with water and dried. The drying step determines that a pharmaceutically acceptable product can be obtained, having a maintenance term of more than 2 years. A very preferred drying method is spray-drying, although the drying can also be suitably carried out using lyophilization.

The process of the present invention will now be further illustrated by the preparation of dextran microspheres using the water-in-water emulsion technique, and by the following, non-limiting examples.

EXAMPLE 1

Polyethylene glycols (PEG) with varying molecular weights were obtained from Merck-Schuchardt, Germany.

Glycidyl methacrylate derivatized dextrans (dex-GMA) with varying DS (degree of substitution; the number of methacrylate groups per 100 glucopyranose residues) were synthesized by a coupling reaction of dextran T40 and glycidyl methacrylate in DMSO (dimethylsulfoxide) using DMAP (N,N-dimethylaminopyridine) as a catalyst, essentially as described by Van Dijk-Wolthuis et al. in Macromolecules 28, (1995) 6317–6322.

Dex-PEG was synthesized as follows. mPEG (monomethoxy-polyethylene glycol, M 5000 g/mmol, 5 g, corresponding with 1 mmol hydroxyl groups) and CDI (carbonyldiimidazole, 162 mg, 1 mmol) were dissolved in 100 ml of anhydrous tetrahydrofuran. The solution was stirred overnight at room temperature, followed by the evaporation of the solvent under reduced pressure. Next, the CI (carbonylimidazole) activated mPEG was added to a solution of dextran T40 (1.7 g) and DMAP (0.35 g) in 50 ml DMSO. This solution was stirred for one week at room temperature. After neutralization of DMAP with HCl, the solution was extensively dialyzed against water and subsequently freeze dried. The product was characterized by gel permeation chromatography and NMR. The degree of substitution amounted to 4 Dex-lactate-HEMA (DS 3) was synthesized as described in the copending European patent application No. 96201821.4.

Polyethylene glycol (PEG, varying molecular weight) was dissolved in 0.22 M KCl to a concentration of 12–40% (w/w). Dex-GMA was dissolved in 0.22 M KCl to a concentration of 10–40% (w/w). Both solutions were flushed with nitrogen for 10 minutes. Next, 4.75 ml of the PEG solution and 0.25 ml of the dex-GMA solution were mixed and vortexed (Winn Vortex-Genie, maximum speed) for 1 minute resulting in a water-in-water emulsion with dextran as the inner phase and PEG as the outer phase. After 10 minutes TEMED ((N,N,N',N'-tetramethylethylenediamine, 100 µl, 20% (v/v) in 0.22 M KCl, pH adjusted with concentrated HCl to 7.2) and KPS (potassium peroxydisulfate, 180 µl, 50 mg/ml in water) were added. The emulsion was incubated for 30 minutes at 37° C. to polymerize the dex-GMA. The microspheres were washed twice with water and freeze dried.

It was demonstrated using in vitro cell cultures that cytotoxicity of dex-GMA is low in similar to the cytotoxicity of dextran, which compound has been used for years as plasma replacing agent in human beings.

The particle size (number weight diameter (=$\Sigma nd/\Sigma n$) and volume weight diameter (=$\Sigma nd^4/\Sigma nd^4$)), I. C. Edmundson, Particle-size analysis, H. S. Bean, A. H. Beckett and J. E. Carles (eds) in: Advances in Pharmaceutical Sciences vol. 2, Academic Press, London 1967, 95–174) and particle size distribution were determined by a laser light blocking technique (Accusizer™, model 770, Particle Sizing Systems, Santa Barbara, Calif. USA). The shape and surface characteristics (porosity) of the microspheres were established by scanning electron microscopy (SEM) analysis.

FIG. 1 gives a representative example of particle size distribution of a dextran microspheres batch prepared via the water-in-water emulsion technique as determined using the Accusizer. SEM analysis showed that the particles are perfectly spherical and non-porous (FIG. 2).

FIG. 3 shows the volume weight average diameter of dextran micropsheres as a function of the degree of GMA substitution and the molecular weight of PEG. The concentration of the PEG solution was 24% (w/w); the concentration of the dex-GMA concentration was 20%. It is shown that the particle size increases with decreasing molecular weight of PEG. At a fixed molecular weight of PEG, the particle size slightly decreases with increasing DS.

FIG. 4 shows the volume weight average diameter of dextran microspheres as a function of the degree of GMA substitution and concentration of the aqueous dex-GMA concentration. The mean diameter decreases with decreasing dex-GMA concentration.

FIG. 5 shows the effect of the concentration and molecular weight of PEG on the volume weight average diameter of the dextran microspheres. For this evaluation, dex-GMA with a DS of 8 in 0.22 M KCl (20%, s/s) was used. It appears that for a given PEG, the largest particles were obtained at a PEG concentration around 24%.

FIG. 6 shows the effect of mixing technique on particle size

EXAMPLE 2

Figure 1:
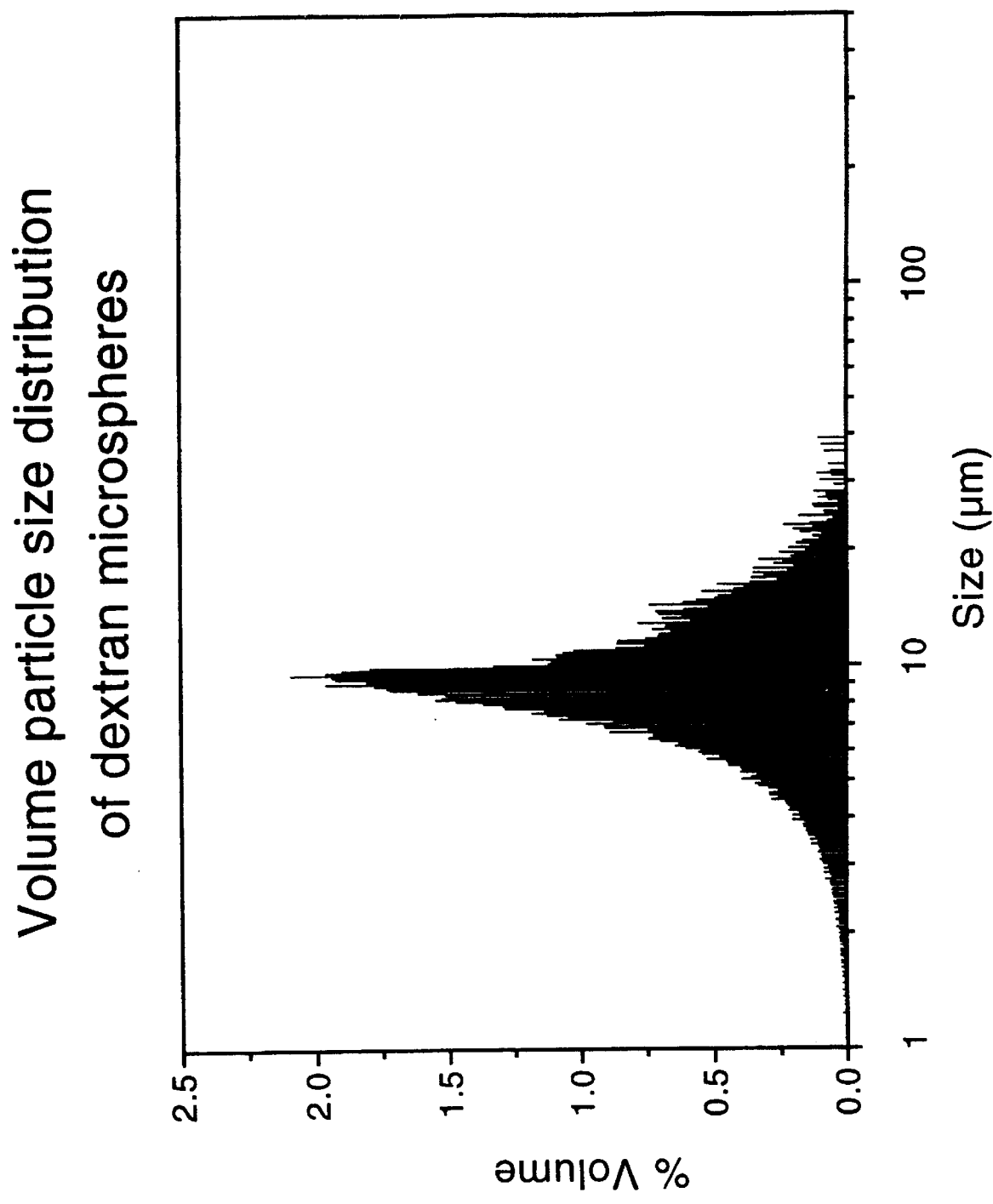
Figure 2:
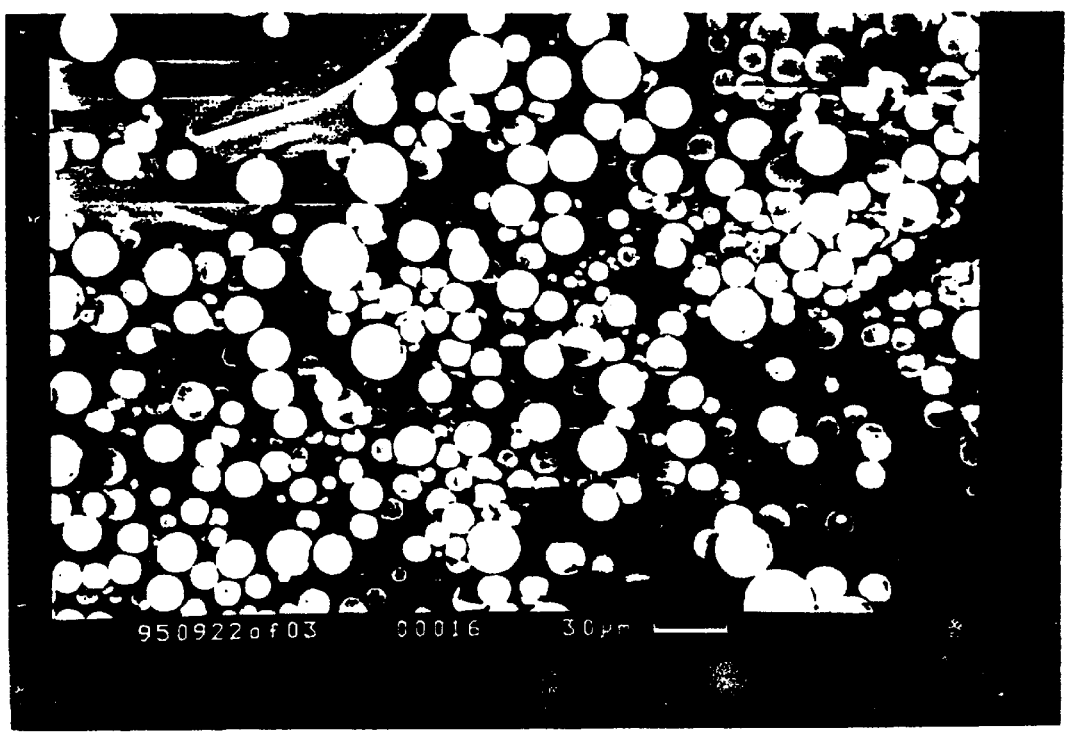
Figure 3:
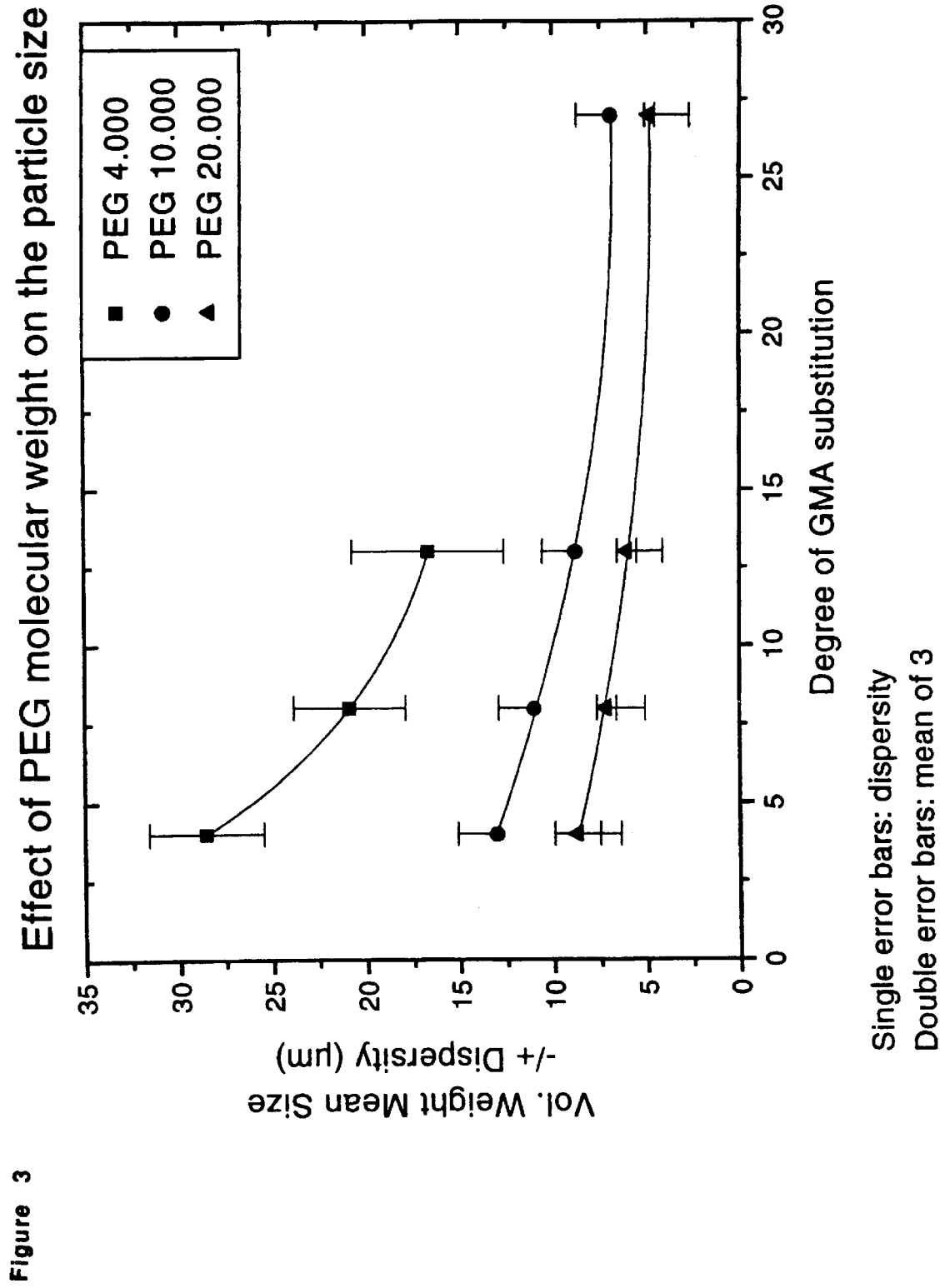
Figure 4:
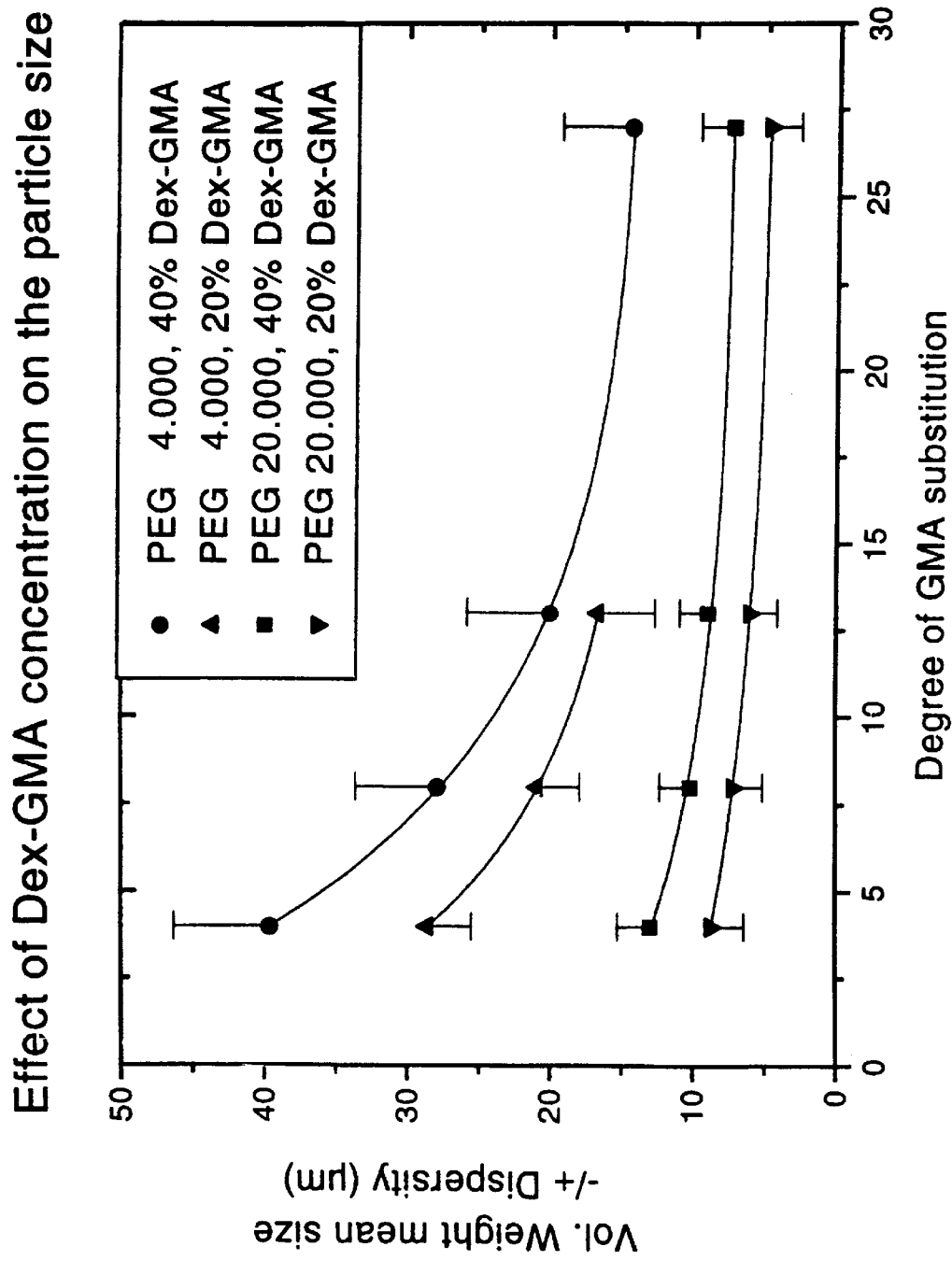
Figure 5:
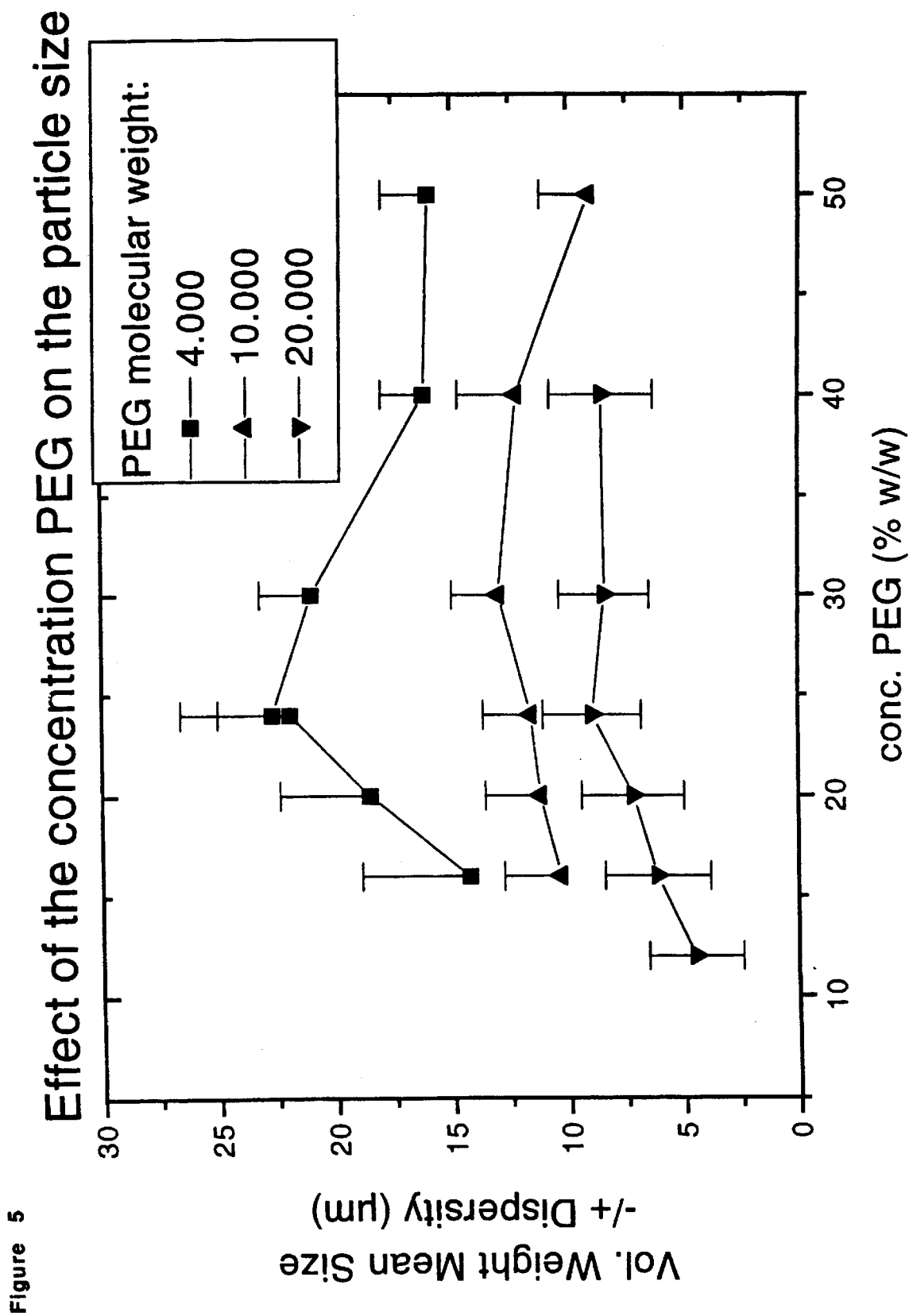

The water-in-water emulsion can also be prepared using a mechanical stirrer instead of the vortex used in Example 1. A solution of dex-GMA (DS 4, 7, 13 or 30; 20% w/w) in 0.22 M KCl was added to a solution of PEG (varying molecular weight; 24%) in 0.22 M KCl, and mechanically stirred (around 600–1000 rpm, depending on the viscosity of the PEG phase) for 5 minutes under a nitrogen stream. Next, TEMED ((N,N,N',N'-tetra-methylethylenediamine, 1.0 ml, 20% (v/v) in 0.22 M KCl, pH adjusted with concentrated HCl to 7.2) and KPS (potassium peroxydisulfate, 1.8 ml, 50 mg/ml in water) were added and the mixture was incubated for 30 minutes at 37° C. to polymerize the dex-GMA. The particle size is slightly greater using a mechanical stirrer instead of a vortex (FIG. 5).

EXAMPLE 3

Microspheres were prepared from the following formulations using the protocol as given in Example 1 and using the following stock solutions:

Stock solutions (% in w/w) in 0.22 M KCl:
  A. PEG 10.000, 24%
  B. PEG 20.000, 24%
  C. Dex-GMA (DS 13) 20%
  D. Dex-lactHEMA (DS 3) 20%
  E. Dex-lactHEMA (DS 3) 10%
  F. Dex-PEG 20%

Table 1 summarizes the results:

| PEG | dex | emulsifier | number weight diameter (µm) | volume weight diameter (µm) |
|---|---|---|---|---|
| 4.50 ml A | 0.25 ml C | 0.25 ml F | 3.3 | 7.2 |
| 4.75 ml A | 0.25 ml C | no | 4.4 | 11.5 |
| 4.75 ml B | 0.25 ml D | no | 6.3 | 17.0 |
| 4.75 ml B | 0.25 ml E | no | 5.3 | 16.0 |

As can be seen, a suitable emulsifier (block-copolymer of dextran and PEG) gives smaller particles with a smaller dispersity (=weight mean diameter/number mean diameter).

EXAMPLE 4

The release of a model protein from non-degrading dextran microspheres and degradable microspheres was evaluated. The microspheres were rendered degradable by the incorporation of dextranase in dex-GMA microspheres.

Dex-GMA (DS 8) was dissolved in 10 mM phosphate buffer pH 8.0. To 2 ml of this solution a fixed amount of IgG (Immunoglobuline G, 25.6 mg) and a variable amount of dextranase (Sigma D1508; 0, 0.1 and 1 U (1 U releases 1 µmol reducing oligosaccharides per minute at 37° C. and pH 6.0)) dextranase were added. This solution was emulsified in an aqueous solution of PEG (M 10.000, concentration 24% (w/w)) in 0.22 M KCl. Thereafter, TEMED (N,N,N',N'-tetramethylethylene-diamine, 100 µl, 20% (v/v) in 0.22 M KCl, pH adjusted with concentrated HCl to 7.2) and KPS (potassium peroxydisulfate, 180 µl, 50 mg/ml in water) were added. The microspheres were washed with water and dried under a nitrogen flow.

Figure 7:
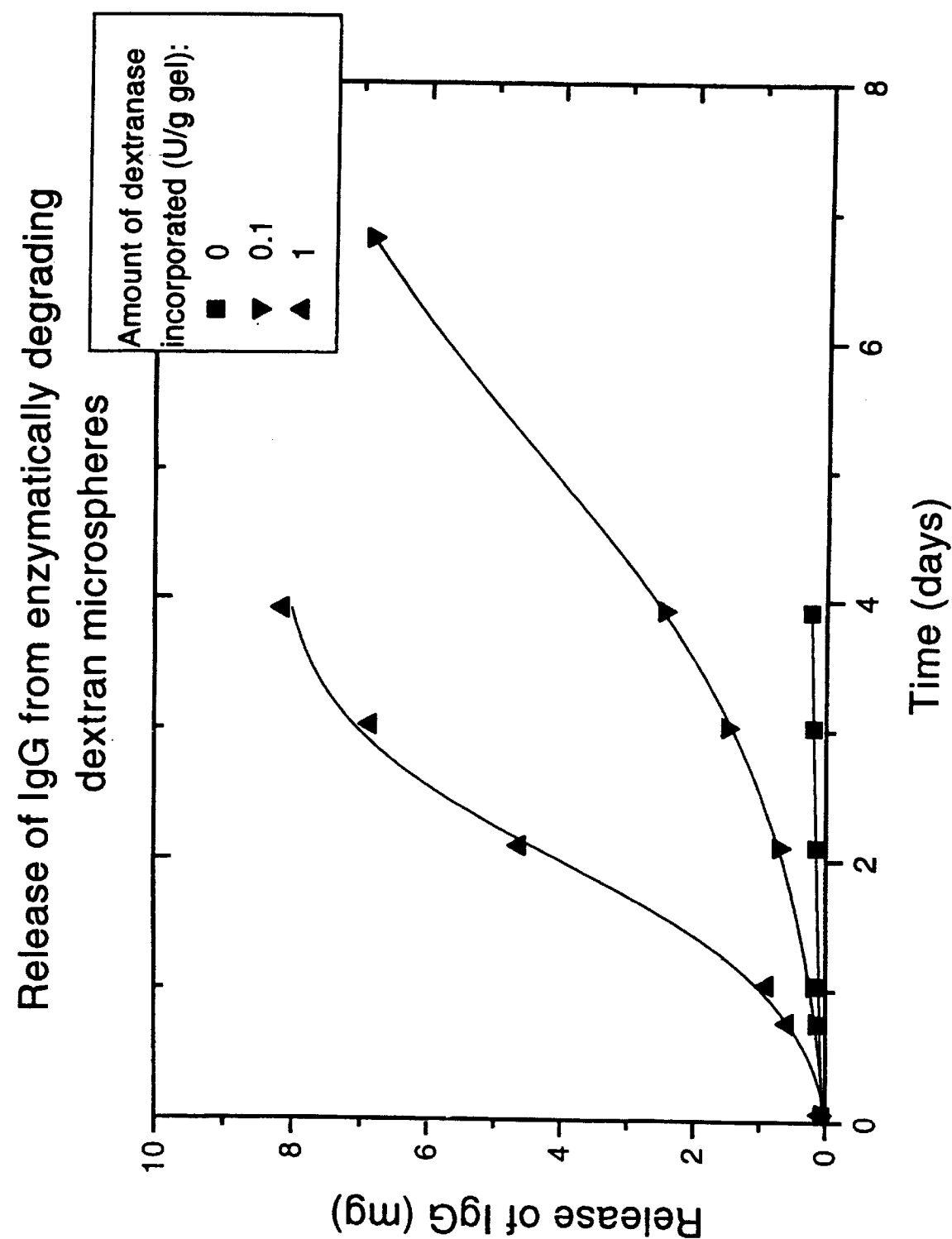
FIG. 7 shows the release of IgG from enzymatically degrading dextran microspheres

An accurately weighed around (0.3–0.5 g) of microspheres was suspended in 10 ml phosphate buffer pH 5.5 and the amount of protein released in the buffer was determined using the biorad protein assay (M. Bradford. Anal. Biochem. 72 (1976) 248–254). FIG. 7 shows the release profiles. From this figure it is clear that the release of IgG from dextran microspheres can be modulated by dextranase.

EXAMPLE 5

The release of a model protein (IgG) from degrading dextran microspheres was evaluated. Degradation was established by co-entrapment of dextranese in the microparticles.

Figure 8:
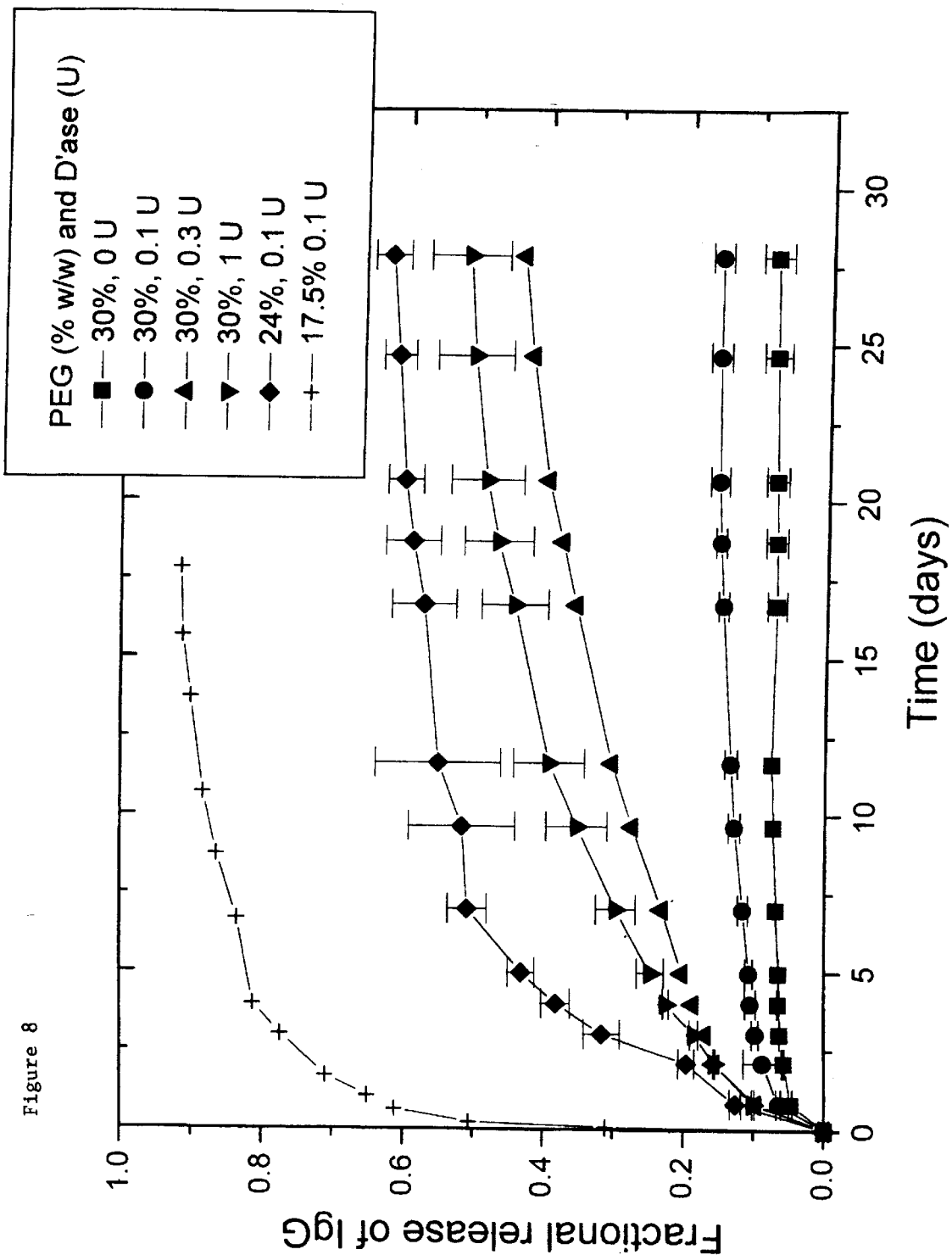
FIG. 8 shows the fractional release of IgG.
Figure 9:
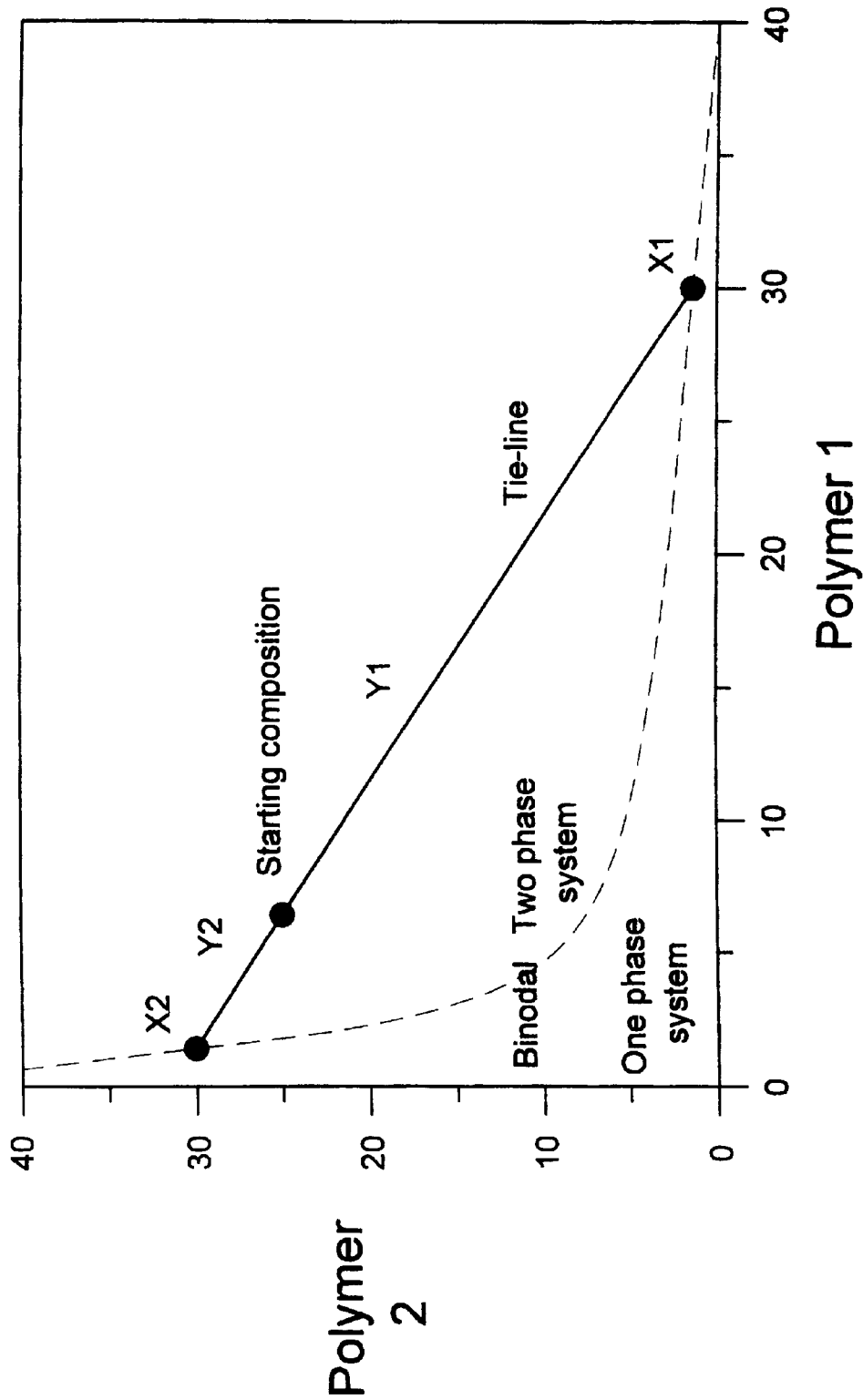
FIG. 9 shows a phase diagram of a water/PEG/dextran ternary system.

Glycidyl methacrylate derivatized dextran (Ds=8; 138 mg) was dissolved in 612 µl buffer (10 mM phosphate, 220 mM KCl, pH 8.0). Thereafter, 250 µl of an aqueous solution of IgG (50 mg/ml) and 250 µl of an aqueous solution of dextranase (variable concentration) were added. IgG and Dextranase were dissolved in the same buffer (10 mM phosphate, 220 mM KCl, pH 8.0). Next, 500 µl of the dexMA, IgG, Dextanase solution was added to 5 ml of an aqueous solution of PEG (molecular weight 10.000 g/mol, concentration 17.5, 24 or 30% w/w) in the same buffer. These phase separated systems were vortexed for 1 minute, followed by the addition of 180 µl potassium peroxodisulphate (50 mg/ml; dissolved in phosphate buffer) and TEMED (N,N,N',N"-tetramethylethylenediamine, 20% v/v, pH adjusted to 8.0 with HCl). Next, the samples were incubated for 30 minutes at 37° C. to polymerize the DexMA. The particles were collected by centrifugation and washed with water. The particles were resuspended in buffer (5 mM NH$_4$Ac, pH 5.5) and incubated at 37° C. Periodically, samples were withdrawn and analyzed for their protein content (Biorad assay). FIG. 8 shows the release profiles. It cen be seen that in the absence of dextgranase the cumulative release was less than 10%, indicating that the hydrodynamic diameter of protein was larger than the hydrogel mesh size. Further, the release rate increases with increasing amount of dextranase in the particles. An increasing amount of dextranase in the particles resulted in an increasing degradation rate. This means that the release of entrapped proteins form dextran particles can be modulated by the degradation rate of the hydrogel matrix. Degradation can be established by addition of an enzyme (dextranase) or by the introduction of hydrolytically labile spacers (e.g. lactate esters) in the crosslinks.

COMPARATIVE EXAMPLE 5 grams of dextran in which the dextran chains are derivated with acryl groups, having a M$_w$ of 40,000, was dissolved in 45 ml of water. A second solution was prepared, with solution comprised 7 g of polyethylene glycol having a M$_w$ of 6,000 in 45 ml water.

At room temperature, the first solution was added to the second solution while stirring. The result was a one phase system, from which no microspheres could be formed. This example illustrates the need to choose the molecular weights and concentrations of the starting materials in such a way that a two-phase system is obtained.

What is claimed is:

1. A method to produce degradable microspheres which effect controlled release of a desired releasable therapeutic substance when in contact with an animal body which method comprises
    (a) providing a ternary two phase system of
        (1) a first water-soluble polymer which is crosslinkable and which, when crosslinked, can be degraded when in contact with an animal body;
        (2) a second water-soluble polymer, and
        (3) water,
    wherein said ternary system is characterized by a phase diagram and wherein said ternary system forms one phase when composition of the ternary system is below the binodal in said phase diagram and forms two phases when the composition of the ternary system is above the binodal in said phase diagram, and wherein the composition of said ternary two phase system provided is above said binodal and is capable of forming a continuous phase and a discontinuous phase;
    (b) forming a continuous and discontinuous phase, wherein said first, crosslinkable, polymer which, when crosslinked, can be degraded when in contact with an animal body is the discontinuous phase in said two-phase system and the second polymer is the continuous phase in said two-phase system, said two phase system having been obtained by adjusting the amounts of water, first polymer and second polymer so as to place the system above the binodal, and
    wherein a releasable therapeutic substance is present in said two-phase system,
    (c) crosslinking said first polymer to form solid degradable microspheres, wherein the degree of crosslinking and water content are adjusted so as to result in pore sizes in said microspheres which are equal to or less than the hydrodynamic diameter of the releasable therapeutic substance, said pores thus entrapping said releasable therapeutic substance, and
    (d) separating the continuous phase from the discontinuous phase to recover the microspheres,
    thus obtaining microspheres which exhibit controlled release of the releasable therapeutic substance when in contact with animal body by effecting expansion of the pores through degradation of said crosslinked first polymer in the animal body.

2. The method of claim 1 wherein the therapeutic substance is a proteinaceous drug, a gene, or a pharmacon.

3. The method of claim 1 wherein said first, crosslinkable polymer, when crosslinked, can be degraded when in contact with the animal body by virtue of comprising bonds that are hydrolyzable under physiological conditions, and said degradation of the crosslinked polymer occurs through hydrolyzing said bonds.

4. The method of claim 1 wherein said first, crosslinkable polymer, when crosslinked, can be degraded by virtue of including, in said microspheres, at least one enzyme which degrades said polymer, and wherein said degradation of crosslinked polymer occurs through action of said enzyme on said polymer.

5. The method of claim 1 wherein the first, crosslinkable polymer is selected from the group consisting of dextran, derivatized dextran, starch, starch derivatives, cellulose derivatives, proteins and derivatized proteins.

6. The method of claim 4 wherein said first, crosslinkable polymer is a dextran or derivatized dextran and the enzyme which degrades that polymer is dextranase.

7. The method of claim 1 wherein the second polymer is polyethylene glycol.

8. The method of claim 1 wherein said crosslinking is formed by crosslinking methacrylate or a methacrylate derivative or by using isocyanate or through poly-N-isopropyl acrylamide.

9. The method of claim 1 wherein step (d) is performed by filtration or centrifugation.

10. Microspheres, at least 80% weight percent thereof having a particle size of between 100 nm and 100 $\mu$m, which microspheres are free of organic solvent, and comprise a degradable, crosslinked polymer encapsulating at least one releasable therapeutic substance, the pore size of the crosslinked polymer being equal to the less than the hydrodynamic diameter of the releasable therapeutic substance, wherein said microspheres effect controlled release of said releasable therapeutic substance when in contact with an animal body.

11. The microspheres of claim 10 wherein 80% of said microspheres have a particle size between 5 and 15 $\mu$m.

12. The microspheres of claim 10 wherein said degradable crosslinked polymer can be degraded when in contact with the animal body by virtue of comprising bonds that are hydrolyzable under physiological conditions.

13. The microspheres of claim 10 which further include an enzyme which degrades said degradable, crosslinked polymer.

14. The microspheres of claim 10 wherein said degradable, crosslinked polymer is selected from the group consisting of dextran, derivatized dextran, starch, starch derivatives, cellulose derivatives, proteins and derivatized proteins.

15. The microspheres of claim 10 wherein said crosslinked polymer is crosslinked by crosslinking methacrylate or a methraylate derivative, or by using isocyanate, or through poly-N-isopropyl acrylamide.

16. The microspheres of claim 13 where said crosslinked polymer is dextran or derivatized dextran and said enzyme is dextranase.

17. The microspheres of claim 10 wherein the therapeutic substance is an proteinaceous drug, a gene, or a pharmacon.

* * * * *